(12) United States Patent
Masuzawa

(10) Patent No.: US 11,983,870 B2
(45) Date of Patent: May 14, 2024

(54) STRUCTURE SEPARATING APPARATUS, STRUCTURE SEPARATING METHOD, AND STRUCTURE SEPARATING PROGRAM, LEARNING DEVICE, LEARNING METHOD, AND LEARNING PROGRAM, AND LEARNED MODEL

(71) Applicant: FUJIFILM Corporation, Tokyo (JP)

(72) Inventor: Naoto Masuzawa, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 399 days.

(21) Appl. No.: 17/496,784

(22) Filed: Oct. 8, 2021

(65) Prior Publication Data
US 2022/0028076 A1 Jan. 27, 2022

Related U.S. Application Data

(63) Continuation of application No. PCT/JP2020/016196, filed on Apr. 10, 2020.

(30) Foreign Application Priority Data

Apr. 11, 2019 (JP) ................................ 2019-075460

(51) Int. Cl.
G06T 7/00 (2017.01)
G06T 5/50 (2006.01)

(52) U.S. Cl.
CPC .............. *G06T 7/0012* (2013.01); *G06T 5/50* (2013.01); *G06T 2207/20081* (2013.01); *G06T 2207/30012* (2013.01)

(58) Field of Classification Search
CPC ...................... G06T 7/0012; G06T 5/50; G06T 2207/20081; G06T 2207/30012
See application file for complete search history.

(56) References Cited

U.S. PATENT DOCUMENTS 11,742,070 B2 * 8/2023 Grady ................. G06F 3/04845
382/278
11,836,997 B2 * 12/2023 Swisher .................... G06T 7/11
(Continued)

FOREIGN PATENT DOCUMENTS

JP H04304580 10/1992
JP 2009531129 9/2009
(Continued)

OTHER PUBLICATIONS

Nikolas Lessmann et al., "Iterative fully convolutional neural networks for automatic vertebra segmentation and dentification," Medical Image Analysis 53, Feb. 2019, pp. 142-155.
(Continued)

*Primary Examiner* — Khai M Nguyen
(74) *Attorney, Agent, or Firm* — JCIPRNET

(57) ABSTRACT

A separation unit that generates a separated image in which a plurality of structures are separated, from an image including the plurality of structures receives an input of an image pair that includes a target image relating to at least a part of the plurality of structures and a non-separation image not including the structure, to output a separation image in which one of the structures is extracted from the target image. The separation unit receives an input of a new image pair including the target image and the separation image, to output a new separation image in which another one of the structures is extracted from the target image. The separation unit repeats the reception of the input of the new image pair including the target image and the new separation image and the output of a new separation image in which another one of the structures is extracted from the target image.

12 Claims, 9 Drawing Sheets

(56) References Cited

U.S. PATENT DOCUMENTS

| | | | |
|---|---|---|---|
| 2009/0169087 A1* | 7/2009 | Doi | G06T 7/0012 |
| | | | 382/132 |
| 2011/0064291 A1 | 3/2011 | Kelm et al. | |
| 2016/0086327 A1* | 3/2016 | Li | G06T 7/0012 |
| | | | 382/128 |
| 2016/0267655 A1* | 9/2016 | Akahori | G06T 7/13 |
| 2019/0108396 A1* | 4/2019 | Dal Mutto | G06V 20/52 |
| 2019/0131012 A1* | 5/2019 | Osawa | G06F 18/22 |

FOREIGN PATENT DOCUMENTS

| | | | | |
|---|---|---|---|---|
| JP | 2016168166 | | 9/2016 | |
| WO | WO-2019032723 A1 * | | 2/2019 | A61B 5/0275 |

OTHER PUBLICATIONS

"International Search Report (Form PCT/ISA/210) of PCT/JP2020/016196," dated Jun. 23, 2020, with English translation thereof, pp. 1-4.

"Written Opinion of the International Searching Authority (Form PCT/ISA/237)" of PCT/JP2020/016196, dated Jun. 23, 2020, with English translation thereof, pp. 1-6.

"Office Action of Japan Counterpart Application" with English translation thereof, dated May 10, 2022, p. 1-p. 7.

* cited by examiner

STRUCTURE SEPARATING APPARATUS, STRUCTURE SEPARATING METHOD, AND STRUCTURE SEPARATING PROGRAM, LEARNING DEVICE, LEARNING METHOD, AND LEARNING PROGRAM, AND LEARNED MODEL

CROSS REFERENCE TO RELATED APPLICATIONS

The present application is a Continuation of PCT International Application No. PCT/JP2020/016196, filed on Apr. 10, 2020, which claims priority to Japanese Patent Application No. 2019-075460, filed on Apr. 11, 2019. Each application above is hereby expressly incorporated by reference, in its entirety, into the present application.

BACKGROUND

Technical Field

The present disclosure relates to a structure separating apparatus, a structure separating method, and a structure separating program, a learning device, a learning method, and a learning program, and a learned model, which separate a plurality of structures included in an image into an individual structure.

Related Art

The spinal cord plays a role in transmitting messages that travel between the brain and each part of the body, and is a very important area. Therefore, the spinal cord is protected by the vertebral column consisting of a plurality of vertebrae. Meanwhile, a tomographic image obtained by scanning a subject is interpreted, and the presence or absence of lesions, such as damage and cancer metastasis, in the vertebrae constituting such a vertebral column is confirmed. Upon the interpretation, it is necessary to identify each vertebra in order to specify the vertebra having the damage and lesion. For this reason, various image processing algorithms have been proposed in which the tomographic image of the subject is acquired, the plurality of vertebrae are separated and recognized on the basis of the acquired tomographic image, and a label is given to each vertebra.

For example, for a medical image obtained from a tomographic image, such as an image of a computed tomography (CT) or an image of a magnetic resonance imaging (MRI), as a target, JP2016-168166A has proposed a method of extracting the vertebrae and the intervertebral disc from the medical image by using a discriminator that has learned to extract the vertebrae and the intervertebral disc, and of specifying the vertebrae by using the feature amounts of the extracted vertebrae and intervertebral disc.

Further, in the literature "Iterative fully convolutional neural networks for automatic vertebra segmentation and identification, Nikolas Lessmann et. al., Medical Image Analysis 53, pp. 142 to 155, 2019" of Lessmann et al., a method has been proposed in which in a case where for a medical image including the vertebrae, a patch that has learned to extract the vertebrae is applied and one vertebra is extracted, the patch is moved on the medical image to sequentially extract the vertebra.

Incidentally, in the method described in JP2016-168166A, it is difficult to label the individual vertebra. Further, in the method described in the literature of Lessmann et al., a patch having a predetermined size is used. For this reason, in a case where the sizes of the vertebrae to be extracted, which are included in the medical image, are different from each other, all the vertebrae cannot be extracted in order and labeled.

SUMMARY OF THE INVENTION

The present disclosure has been made in view of the above circumstances, and an object thereof is to enable accurate separation of a plurality of structures, such as vertebrae, included in an image.

There is provided a structure separating apparatus according to the present disclosure comprising a separation unit that generates a separated image in which a plurality of structures are separated, from an image including the plurality of structures, in which the separation unit
receives an input of an image pair that includes a target image relating to at least a part of the plurality of structures and a non-separation image not including the structure, to output a separation image in which one of the structures is extracted from the target image,
receives an input of a new image pair including the target image and the separation image, to output a new separation image in which another one of the structures is extracted from the target image, and
repeats the reception of the input of the new image pair including the target image and the new separation image and the output of a new separation image in which another one of the structures is extracted from the target image, to generate the separated image in which the plurality of structures included in the target image are separated.

In the structure separating apparatus according to the present disclosure, the separation unit may have a learned model that has learned to receive an input of an image pair that includes a target image including at least a part of the plurality of structures and a non-separation image not including the structure, to output a separation image in which one of the structures is extracted from the target image,
receive an input of a new image pair including the target image and the separation image, to output a new separation image in which another one of the structures is extracted from the target image, and
repeat the reception of the input of the new image pair including the target image and the new separation image and the output of a new separation image in which another one of the structures is extracted from the target image, to generate the separated image in which the plurality of structures included in the target image are separated.

Further, in the structure separating apparatus according to the present disclosure, a labeling unit that labels a plurality of the separated structures in an order of separation may further be provided.

Further, in the structure separating apparatus according to the present disclosure, a display control unit that displays the image or the target image including the labeled structure, on a display unit may further be provided.

Further, in the structure separating apparatus according to the present disclosure, the structure may be a vertebra.

Further, in the structure separating apparatus according to the present disclosure, a target image generation unit that classifies a plurality of the vertebrae into cervical vertebrae, thoracic vertebrae, and lumbar vertebrae, and generates the target image relating to at least one of the cervical vertebrae, the thoracic vertebrae, or the lumbar vertebrae may further be provided.

There is provided a learning device according to the present disclosure, in which the learning device receives an input of an image pair that includes a target image including at least a part of a plurality of structures and a non-separation image not including the structure, to output a separation image in which one of the structures is extracted from the target image,
   receives an input of a new image pair including the target image and the separation image, to output a new separation image in which another one of the structures is extracted from the target image, and
   repeats the reception of the input of the new image pair including the target image and the new separation image and the output of a new separation image in which another one of the structures is extracted from the target image, to generate a learned model that generates a separated image in which the plurality of structures included in the target image are separated.

There is a learned model according to the present disclosure, in which the learned model receives an input of an image pair that includes a target image including at least a part of a plurality of structures and a non-separation image not including the structure, to output a separation image in which one of the structures is extracted from the target image,
   receives an input of a new image pair including the target image and the separation image, to output a new separation image in which another one of the structures is extracted from the target image, and
   repeats the reception of the input of the new image pair including the target image and the new separation image and the output of a new separation image in which another one of the structures is extracted from the target image, to generate a separated image in which the plurality of structures included in the target image are separated.

There is provided a structure separating method according to the present disclosure of generating a separated image in which a plurality of structures are separated, from an image including the plurality of structures, the structure separating method comprising:
   receiving an input of an image pair that includes a target image relating to at least a part of the plurality of structures and a non-separation image not including the structure, to output a separation image in which one of the structures is extracted from the target image;
   receiving an input of a new image pair including the target image and the separation image, to output a new separation image in which another one of the structures is extracted from the target image; and
   repeating the reception of the input of the new image pair including the target image and the new separation image and the output of a new separation image in which another one of the structures is extracted from the target image, to generate the separated image in which the plurality of structures included in the target image are separated.

There is provided a learning method according to the present disclosure comprising:
   receiving an input of an image pair that includes a target image including at least a part of a plurality of structures and a non-separation image not including the structure, to output a separation image in which one of the structures is extracted from the target image;
   receiving an input of a new image pair including the target image and the separation image, to output a new separation image in which another one of the structures is extracted from the target image; and
   repeating the reception of the input of the new image pair including the target image and the new separation image and the output of a new separation image in which another one of the structures is extracted from the target image, to generate a learned model that generates a separated image in which the plurality of structures included in the target image are separated.

The structure separating method and the learning method according to the present disclosure may be provided as programs to be executed by a computer.

There is provided another structure separating apparatus according to the present disclosure comprising a memory that stores a command to be executed by a computer; and
   a processor configured to execute the stored command, in which the processor executes processing of
   generating a separated image in which a plurality of structures are separated, from an image including the plurality of structures, the processor executing processing of
      receiving an input of an image pair that includes a target image relating to at least a part of the plurality of structures and a non-separation image not including the structure, to output a separation image in which one of the structures is extracted from the target image,
      receiving an input of a new image pair including the target image and the separation image, to output a new separation image in which another one of the structures is extracted from the target image, and
      repeating the reception of the input of the new image pair including the target image and the new separation image and the output of a new separation image in which another one of the structures is extracted from the target image, to generate the separated image in which the plurality of structures included in the target image are separated.

There is provided another learning device according to the present disclosure comprising a memory that stores a command to be executed by a computer; and
   a processor configured to execute the stored command, in which the processor executes processing of
      receiving an input of an image pair that includes a target image including at least a part of a plurality of structures and a non-separation image not including the structure, to output a separation image in which one of the structures is extracted from the target image,
      receiving an input of a new image pair including the target image and the separation image, to output a new separation image in which another one of the structures is extracted from the target image, and
      repeating the reception of the input of the new image pair including the target image and the new separation image and the output of a new separation image in which another one of the structures is extracted from the target image, to generate a learned model that generates a separated image in which the plurality of structures included in the target image are separated.

According to the present disclosure, a plurality of structures, such as vertebrae, included in an image can be accurately separated.

DETAILED DESCRIPTION

Figure 1:
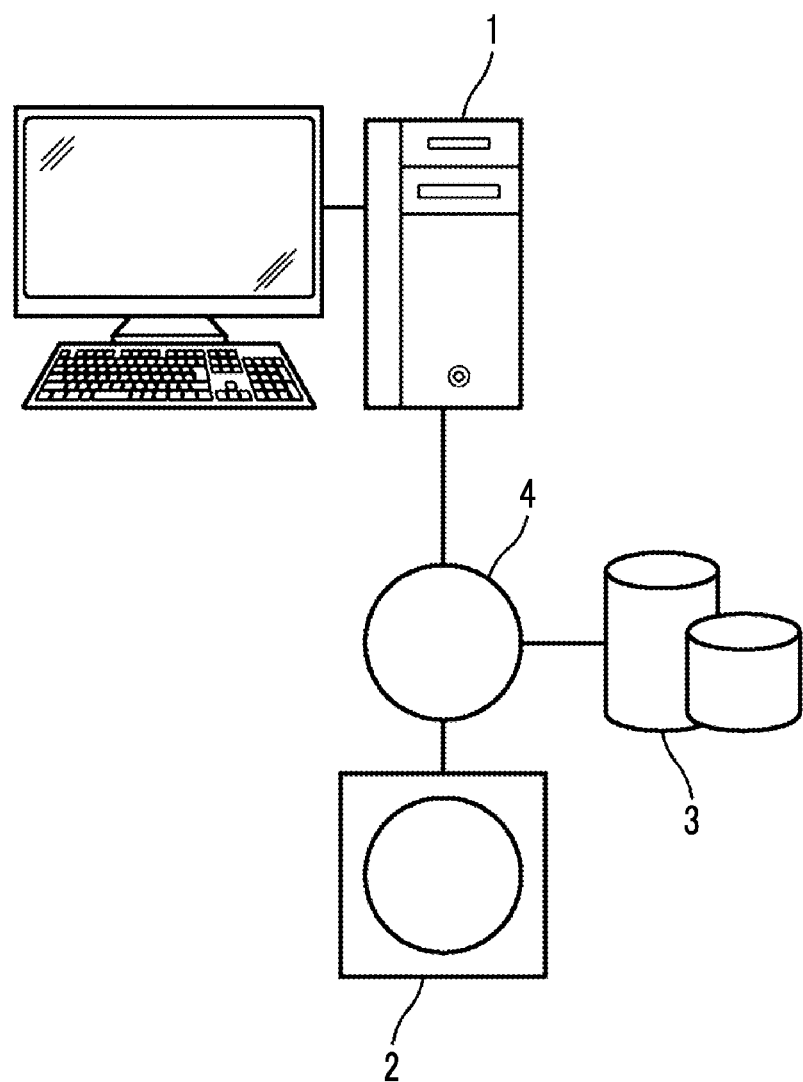
FIG. 1 is a hardware configuration diagram showing an outline of a diagnosis support system to which a structure separating apparatus according to an embodiment of the present disclosure is applied.

Hereinafter, an embodiment of the present disclosure will be described with reference to the drawings. FIG. 1 is a hardware configuration diagram showing an outline of a diagnosis support system to which a structure separating apparatus and a learning device according to the embodiment of the present disclosure are applied. As shown in FIG. 1, in the system, a structure separating apparatus 1, a three-dimensional image capturing apparatus 2, and an image storage server 3 according to the present embodiment are connected to communicate with one another via a network 4.

The three-dimensional image capturing apparatus 2 is an apparatus that images an area to be diagnosed of a subject and generates a three-dimensional image representing the area, and specific examples thereof include a CT apparatus, an MM apparatus, and a positron emission tomography (PET) apparatus. The three-dimensional image generated by the three-dimensional image capturing apparatus 2 is transmitted to and stored in the image storage server 3. In the present embodiment, it is assumed that the area to be diagnosed of the subject is the vertebral column, the three-dimensional image capturing apparatus 2 is an MRI apparatus, and the three-dimensional image is an MRI image of the vertebral column of the subject. A plurality of vertebrae constituting the vertebral column correspond to a plurality of structures.

The image storage server 3 is a computer that stores and manages various data, and comprises a large-capacity external storage device and database management software. The image storage server 3 communicates with another apparatus via a wired or wireless network 4 to transmit and receive image data and the like. Specifically, the image storage server 3 acquires the image data, such as the three-dimensional image generated by the three-dimensional image capturing apparatus 2, via the network, and stores and manages the acquired image data in a recording medium, such as a large-capacity external storage device. A storage format of the image data and communication between the apparatuses via the network 4 are based on a protocol such as digital imaging and communication in medicine (DI-COM). Further, a tag based on the DICOM standard is given to the three-dimensional image. The tag includes information, such as a patient name, information representing an imaging apparatus, an imaging date and time, and an imaging area.

The structure separating apparatus 1 incorporates a learning device according to the present embodiment, and is an apparatus obtained by installing a structure separating program and a learning program according to the present disclosure on one computer. The computer may be a workstation or a personal computer directly operated by a doctor who makes diagnosis, or may be a server computer connected to the workstation or the personal computer via the network. The structure separating program is stored in a storage device of a server computer connected to the network or a network storage so as to be accessible from the outside, and is downloaded and installed on the computer that the doctor uses according to a request. Alternatively, the structure separating program is recorded in a recording medium, such as a digital versatile disc (DVD) or a compact disc read only memory (CD-ROM), and distributed, and is installed on a computer from the recording medium.

Figure 2:
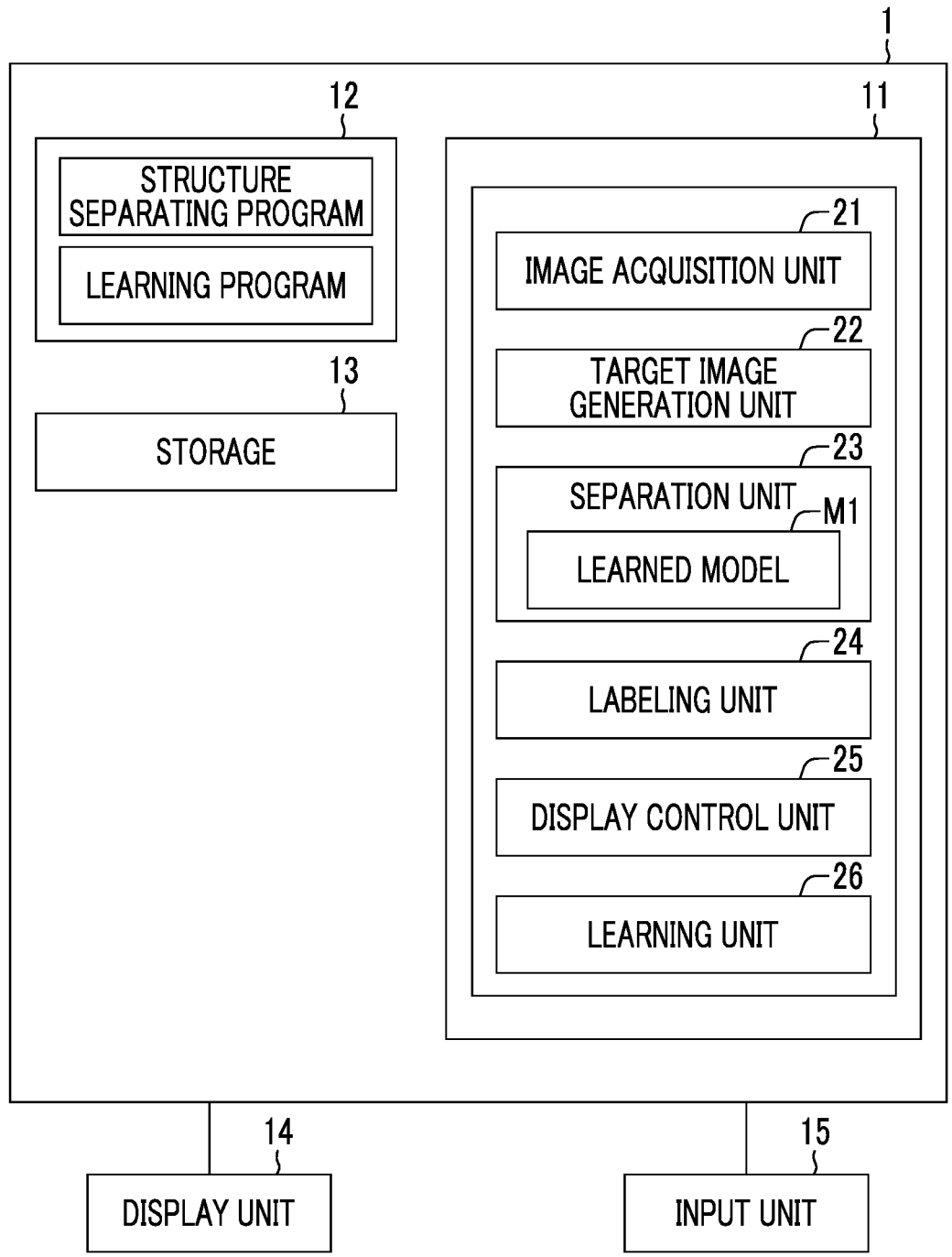
FIG. 2 is a diagram showing a schematic configuration of the structure separating apparatus which is realized with a structure separating program installed on a computer.

FIG. 2 is a diagram showing a schematic configuration of the structure separating apparatus which is realized with the structure separating program and the learning program installed on a computer. As shown in FIG. 2, the structure separating apparatus 1 comprises a CPU 11, a memory 12, and a storage 13, as a standard workstation configuration. Further, a display unit 14, such as a liquid crystal display, and an input unit 15, such as a mouse, are connected to the structure separating apparatus 1. A touch panel that serves as the display unit 14 and the input unit 15 may be used.

The storage 13 stores various information including a three-dimensional image acquired from the image storage server 3 via the network 4 and an image generated by processing by the structure separating apparatus 1.

Further, the structure separating program and the learning program are stored in the memory 12. The structure separating program defines, as processing to be executed by the CPU 11, image acquiring processing of acquiring a three-dimensional image to be processed, target image generating processing of classifying a plurality of vertebrae included in the three-dimensional image into the cervical vertebrae, the thoracic vertebrae, and the lumbar vertebrae and generating a target image relating to at least one of the cervical vertebrae, the thoracic vertebrae, or the lumbar vertebrae, separating processing of generating a separated image in which the plurality of vertebrae included in the target image are separated, labeling processing of labeling the plurality of separated vertebrae in the order of separation, and display controlling processing of displaying a medical image or the target image including the labeled vertebrae, on the display unit 14. The learning program defines learning processing for generating a learned model, which will be described later, as processing to be executed by the CPU 11.

The CPU 11 executes the processing according to the programs, so that the computer functions as an image acquisition unit 21, a target image generation unit 22, a separation unit 23, a labeling unit 24, a display control unit 25, and a learning unit 26.

The image acquisition unit 21 includes an interface connected to the network, and acquires a three-dimensional image V0 to be processed including the vertebral column, from the image storage server 3. In a case where the three-dimensional image V0 is already stored in the storage 13, the image acquisition unit 21 may acquire the three-dimensional image V0 from the storage 13. In the present embodiment, it is assumed that the three-dimensional image V0 includes the entire vertebral column of the subject.

The target image generation unit 22 generates a target image, as a vertebrae separation target by the separation unit 23, which will be described later. In the present embodiment, the three-dimensional image V0 includes the entire vertebral column of the subject. Therefore, the target image generation unit 22 classifies the plurality of vertebrae constituting the vertebral column into the cervical vertebrae, the thoracic vertebrae, and the lumbar vertebrae, and generates a target image relating to at least one of the cervical vertebrae, the thoracic vertebrae, or the lumbar vertebrae. The target image includes a part of the vertebral column. The target image may be a three-dimensional image, but may be a two-dimensional tomographic image of a sagittal cross-section or a coronal cross-section along the vertebral column. In the present embodiment, the target image is a two-dimensional tomographic image.

Figure 3:
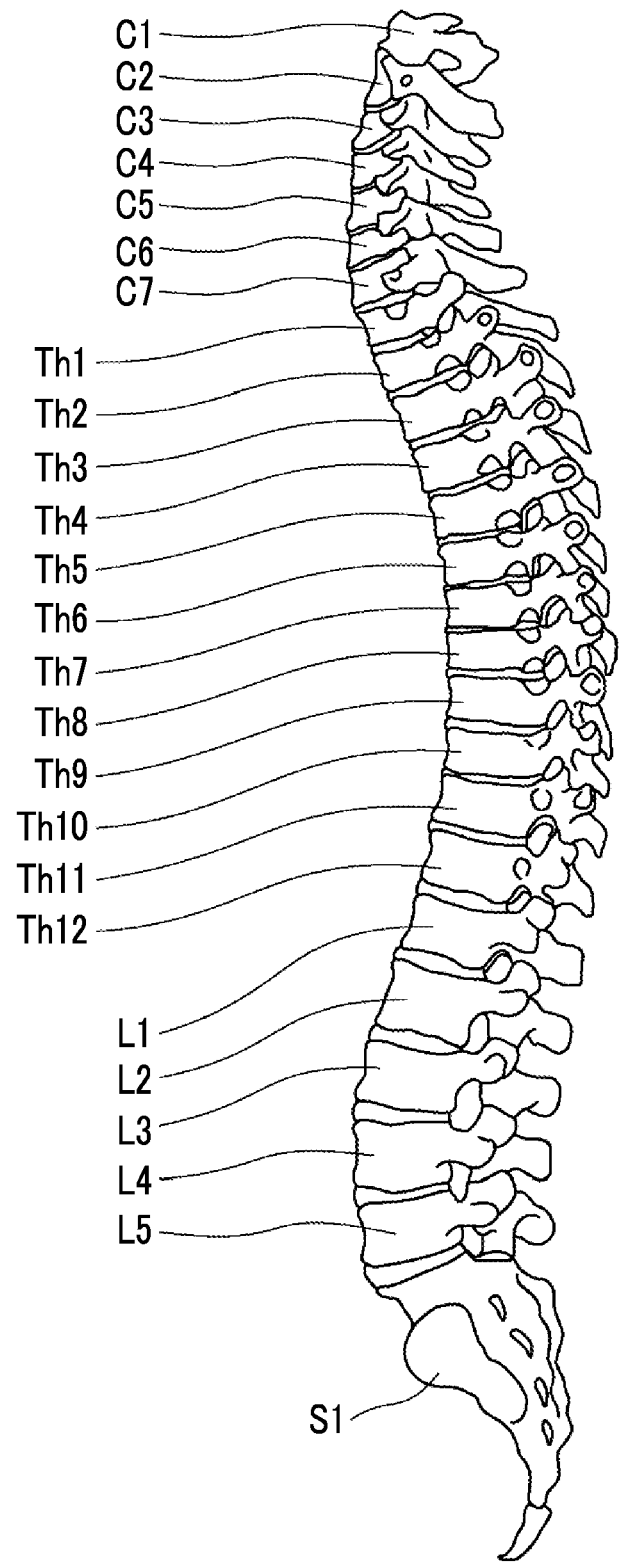
FIG. 3 is a diagram schematically showing a standard arrangement of vertebrae.

FIG. 3 is a diagram schematically showing a standard arrangement of the plurality of vertebrae constituting the vertebral column. As shown in FIG. 3, each vertebra is anatomically labeled. Here, the vertebral column consists of four parts of the cervical vertebrae, the thoracic vertebrae, the lumbar vertebrae, and the sacrum. The cervical vertebrae consist of seven vertebrae and are anatomically labeled C1 to C7. The thoracic vertebrae consist of twelve vertebrae and are anatomically labeled Th1 to Th12. The lumbar vertebrae consist of five vertebrae and are anatomically labeled L1 to L5. The sacrum consists of only one bone and is anatomically labeled S1. In some people, the numbers of the cervical vertebrae, the thoracic vertebrae, and the lumbar vertebrae, as well as the total number of vertebrae, may differ from the number of the standard vertebral column described above. In the present embodiment, the vertebrae included in the three-dimensional image V0 are separated in order to perform labeling as shown in FIG. 3.

In the present embodiment, the target image generation unit 22 classifies the seven vertebrae into the cervical vertebrae, the twelve vertebrae into the thoracic vertebrae, and the five vertebrae into the lumbar vertebrae, for example, in order from the top in the three-dimensional image V0, and generates a target image as a vertebrae classification target. In the present embodiment, a target image G1 as a vertebrae classification target of the lumbar vertebrae is generated, but the present embodiment is not limited thereto. A target image including the cervical vertebrae, the thoracic vertebrae, and the lumbar vertebrae, or a combination of two of the cervical vertebrae, the thoracic vertebrae, and the lumbar vertebrae may be generated.

Here, in the present embodiment, the target image generation unit 22 has a learned model that has learned, in a case where the input of the three-dimensional image V0 including the plurality of vertebrae is received, to classify the plurality of vertebrae into the cervical vertebrae, the thoracic vertebrae, and the lumbar vertebrae. As the learned model, for example, a convolutional neural network (CNN) may be used, but the learned model is not limited thereto. In addition to the CNN, a support vector machine (SVM), a deep neural network (DNN), a recurrent neural network (RNN), and the like may be used.

The target image generation unit 22 is not limited to a unit provided with the learned model. Since, among the plurality of vertebrae constituting the vertebral column, the sacrum has a characteristic shape, the sacrum may be specified by template matching using the sacrum, and the plurality of vertebrae may be classified into the cervical vertebrae, the thoracic vertebrae, and the lumbar vertebrae, on the basis of the sacrum. Further, the target image generation unit 22 may generate the target image, by using the result in which an operator observes the three-dimensional image V0 and manually classifies the plurality of vertebrae into the cervical vertebrae, the thoracic vertebrae, the lumbar vertebrae.

Figure 4:
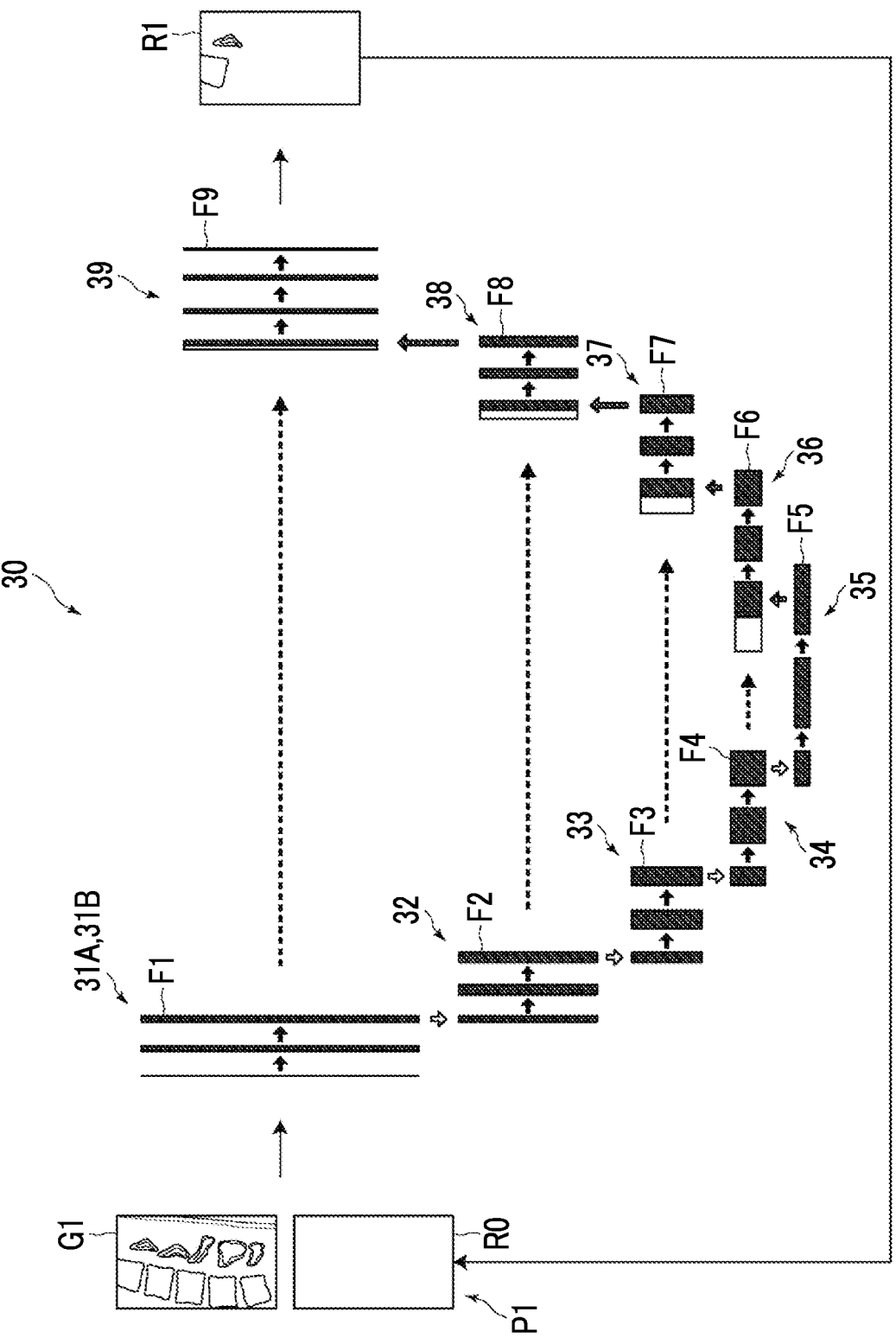
FIG. 4 is a diagram schematically showing a configuration of a learned model.

The separation unit 23 generates a separated image in which the plurality of vertebrae are separated in the target image G1. For the separated image, the separation unit 23 has a learned model that has learned to separate the plurality of vertebrae included in the image. FIG. 4 is a diagram schematically showing the configuration of the learned model. As shown in FIG. 4, a learned model M1 included in the separation unit 23 in the present embodiment is constituted of U-Net, which is one type of neural networks. The U-Net 30 shown in FIG. 4 has first convolutional layer groups 31A and 31B and a second to ninth convolutional layer groups 32 to 39. As shown in FIG. 4, since the shape of the connection between the first convolutional layer groups 31A and 31B and the second to ninth convolutional layer groups 32 to 39 is U-shaped, the neural network is called U-Net.

In the present embodiment, the input of a first image pair P1 including the target image G1 and a non-separation image R0 not including the vertebra are received to each of the first convolutional layer groups 31A and 31B. The non-separation image R0 is an image which has the same size as the target image G1 and in which nothing is drawn. The first convolutional layer groups 31A and 31B each have two convolutional layers, and a feature map F1 in which two feature maps after convolution are integrated is output. The input of the integrated feature map F1 is received to the ninth convolutional layer group 39 as shown by the broken line in FIG. 4. In addition, the integrated feature map F1 is pooled, reduced in size by half, and received to the second convolutional layer group 32 as an input. In FIG. 4, the pooling is indicated by the downward arrow. In the present embodiment, for example, a 3×3 kernel is used for convolution, but the present disclosure is not limited thereto. Further, the maximum value among the four pixels is adopted for the pooling, but the present disclosure is not limited thereto.

The second convolutional layer group 32 has two convolutional layers, and the input of a feature map F2 output from the second convolutional layer group 32 is received to the eighth convolutional layer group 38, as shown by the broken line in FIG. 4. Further, the feature map F2 is pooled, reduced in size by half, and received to the third convolutional layer group 33 as an input.

The third convolutional layer group 33 also has two convolutional layers, and the input of a feature map F3 output from the third convolutional layer group 33 is received to the seventh convolutional layer group 37, as shown by the broken line in FIG. 4. Further, the feature map F3 is pooled, reduced in size by half, and received to the fourth convolutional layer group 34 as an input.

The fourth convolutional layer group 34 also has two convolutional layers, and the input of a feature map F4 output from the fourth convolutional layer group 34 is received to the sixth convolutional layer group 36, as shown by the broken line in FIG. 4. Further, the feature map F4 is pooled, reduced in size by half, and received to the fifth convolutional layer group 35 as an input.

The fifth convolutional layer group 35 has one convolutional layer, and a feature map F5 output from the fifth convolutional layer group 35 is upsampled, doubled in size, and received to the sixth convolutional layer group 36 as an input. In FIG. 4, the upsampling is indicated by the upward arrow.

The sixth convolutional layer group 36 has two convolutional layers, and integrates the feature map F4 from the fourth convolutional layer group 34 and the upsampled feature map F5 from the fifth convolutional layer group 35 to perform the convolution operation. A feature map F6 output from the sixth convolutional layer group 36 is upsampled, doubled in size, and received to the seventh convolutional layer group 37 as an input.

The seventh convolutional layer group 37 has two convolutional layers, and integrates the feature map F3 from the third convolutional layer group 33 and the upsampled feature map F6 from the sixth convolutional layer group 36 to perform the convolution operation. A feature map F7 output from the seventh convolutional layer group 37 is upsampled and received to the eighth convolutional layer group 38 as an input.

The eighth convolutional layer group 38 has two convolutional layers, and integrates the feature map F2 from the second convolutional layer group 32 and the upsampled feature map F7 from the seventh convolutional layer group 37 to perform the convolution operation. A feature map F8 output from the eighth convolutional layer group 38 is upsampled and received to the ninth convolutional layer group 39 as an input.

The ninth convolutional layer group 39 has three convolutional layers, and integrates the feature map F1 from the first convolutional layer groups 31A and 31B and the upsampled feature map F8 from the eighth convolutional layer group 38 to perform the convolution operation. A feature map F9 output from the ninth convolutional layer group 39 is a separation image R1 in which the first vertebra 61 is extracted in the target image G1.

In the present embodiment, the input of the separation image R1 is recursively received to the first convolutional layer groups 31A and 31B as a second image pair P2 together with the target image G1, in order to separate the next vertebra. Thereby, a separation image R2 in which the second vertebra 62 adjacent to the vertebra 61 is extracted in the target image G1 is output. The input of the separation image R2 is recursively received to the first convolutional layer groups 31A and 31B as a third image pair P3 together with the target image G1, in order to separate the next vertebra. Then, the separation unit 23 repeats the above processing until all the vertebrae are separated.

Figure 5:
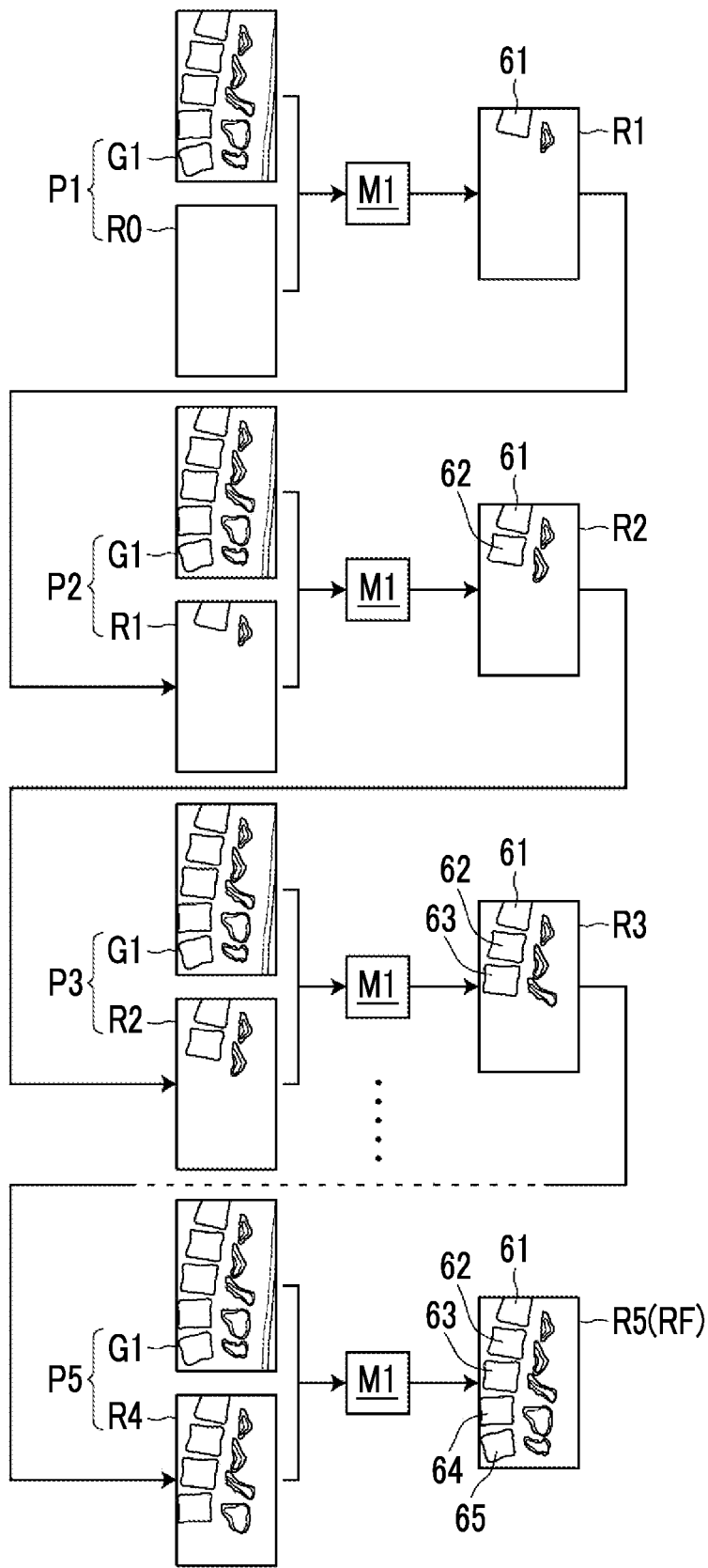
FIG. 5 is a diagram schematically showing processing for generating a separated image performed in the present embodiment.

FIG. 5 is a diagram schematically showing processing for generating a separated image performed in the present embodiment. As described above, in the first processing, in a case where the input of the first image pair P1 including the target image G1 and the non-separation image R0 is first received to the learned model M1, the separation image R1 in which the first vertebra 61 is extracted is output from the learned model M1. Next, in a case where the input of the second image pair P2 including the target image G1 and the separation image R1 is received to the learned model M1, the separation image R2 in which the second vertebra 62 is extracted is output from the learned model M1. Next, in a case where the input of the third image pair P3 including the target image G1 and the separation image R2 is received to the learned model M1, a separation image R3 in which the third vertebra 63 is extracted is output from the learned model M1. Next, although illustration is omitted in FIG. 5, in a case where the input of a fourth image pair P4 including the target image G1 and the separation image R3 is received to the learned model M1, a separation image R4 in which the fourth vertebra 64 is extracted is output from the learned model M1. Then, in a case where the input of a fifth image pair P5 including the target image G1 and the separation image R4 is received to the learned model M1, the separation image R5 in which all the vertebrae 61 to 65 included in the target image G1 are extracted is output as a separated image RF.

As described above, in the present embodiment, in a case where the learned model M1 constituting the separation unit 23 includes n vertebrae in the target image G1, the input of an i-th (i=1 to n−1) image pair including the target image G1 and the separation image Ri is recursively received, and the separated image RF in which n vertebrae are separated in the target image G1 is generated.

The labeling unit 24 labels the separated vertebrae in the order of separation on the basis of the separated image RF. In the present embodiment, since the target image G1 is an image of the lumbar vertebrae, the labeling unit 24 assigns labels L1 to L5 to the separated vertebrae in the order of separation.

Figure 6:
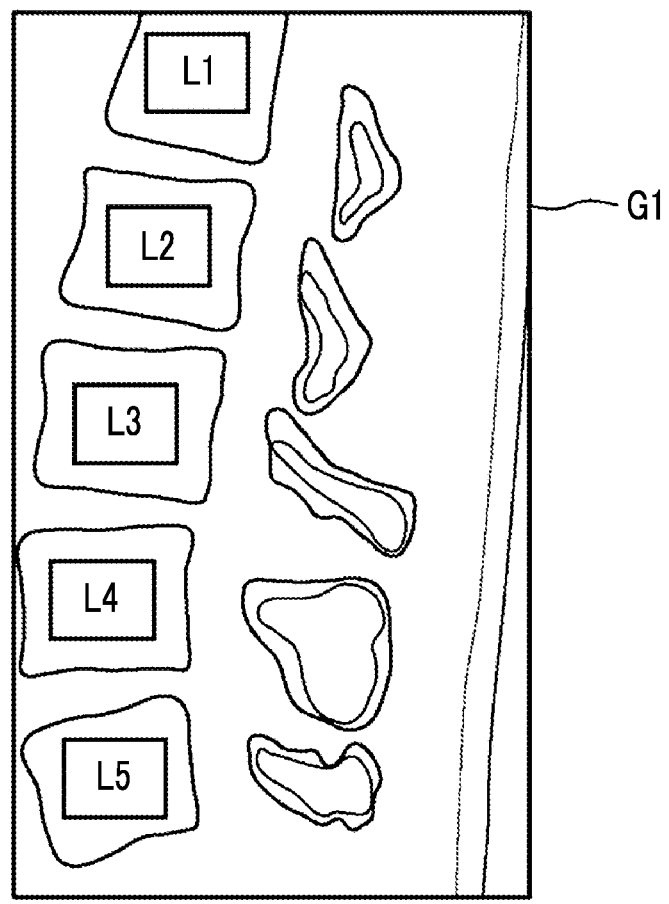
FIG. 6 is a diagram showing a labeled target image.

The display control unit 25 displays the target image G1 including the labeled vertebrae on the display unit 14. FIG. 6 is a diagram showing the target image G1 including the labeled vertebrae displayed on the display unit 14. Since the target image G1 is an image of the lumbar vertebrae, as shown in FIG. 6, in the displayed target image G1, labels L1 to L5 are assigned from the top in the order of separation.

The learning unit 26 generates the learned model included in the separation unit 23. The learning unit 26 performs learning of the U-Net 30 using a large number of training data, and generates the learned model M1. The input of the training data is received from the input unit 15. In the present embodiment, a set of three images that include a first image including the vertebrae, a second image in which 0 or more of the vertebrae included in the image including the vertebrae are extracted, and a third image in which the extracted vertebrae is one more in number than the second image is used as the training data.

Figure 7:
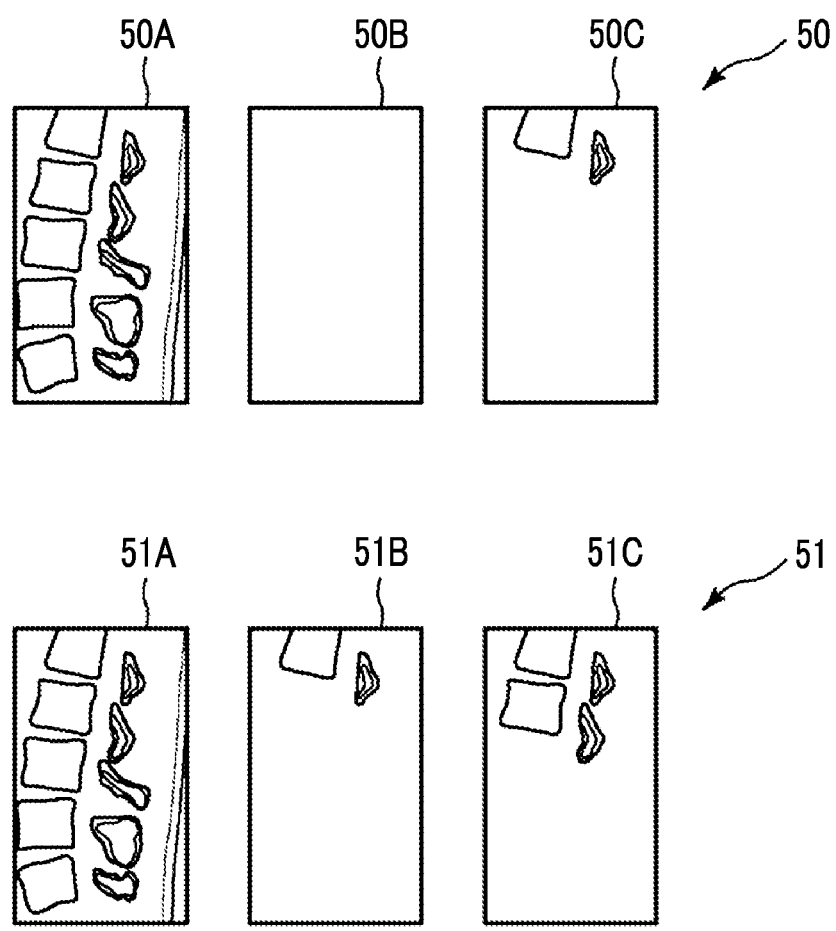
FIG. 7 is a diagram showing an example of training data.

FIG. 7 is a diagram showing an example of the training data. As shown in FIG. 7, the training data 50 includes a first image 50A including the vertebrae of the subject, a second image 50B that has the same size as the first image 50A and is a non-separation image in which nothing is extracted, and a third image 50C in which one vertebra is extracted in the first image 50A. The learning unit 26 uses the training data 50, thereby learning to receive the input of the image pair that includes the image (that is, the target image) including the plurality of vertebrae and the non-separation image in which nothing is extracted, to output the separation image in which the first vertebra is separated.

On the other hand, the training data 51 shown in FIG. 7 includes a first image 51A including the vertebrae of the subject, a second image 51B which has the same size as the first image 51A and in which one vertebra is extracted, and a third image 51C in which two vertebrae are extracted in the first image 51A. The learning unit 26 uses the training data 51, thereby learning to receive the input of the image pair that includes the target image including the plurality of vertebrae and the separation image in which one vertebra is extracted, to output the separation image in which the second vertebra adjacent to the first vertebra is separated.

As described above, the learned model M1 according to the present embodiment has learned to receive the input of the image pair that includes the target image including the plurality of vertebrae and the non-separation image not including the vertebra to output the separation image in which one of the vertebrae is extracted from the target image, receive the input of a new image pair including the target image and the separation image to output a new separation image in which another one of the vertebrae is extracted from the target image, and repeat the reception of the input of the new image pair including the target image and the new separation image and the output of a new separation image in which another one of the vertebrae is extracted from the target image to generate a separated image RF in which the plurality of vertebrae included in the target image G1 are separated.

Figure 8:
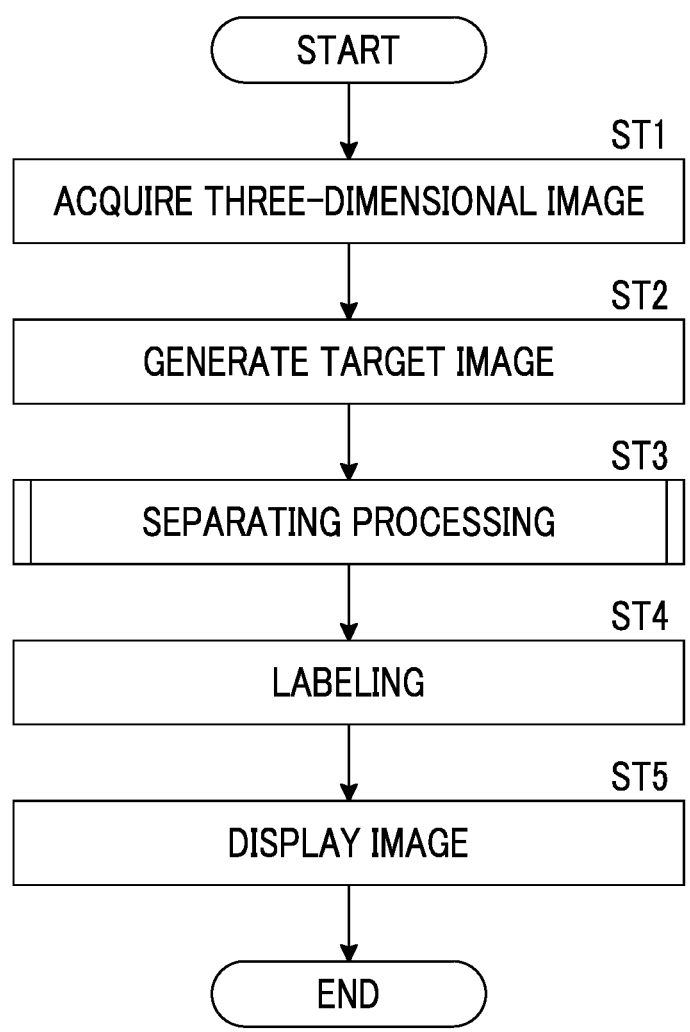
FIG. 8 is a flowchart of structure separating processing in the present embodiment.

Next, processing performed in the present embodiment will be described. FIG. 8 is a flowchart of structure separating processing in the present embodiment. First, the image acquisition unit 21 acquires the three-dimensional image V0 to be diagnosed from the image storage server 3 (Step ST1), and the target image generation unit 22 generates the target image G1, as a vertebrae separation target, from the three-dimensional image V0 (Step ST2). Subsequently, the separation unit 23 performs separating processing of generating the separated image RF in which the plurality of vertebrae are separated in the target image G1 (Step ST3).

Figure 9:
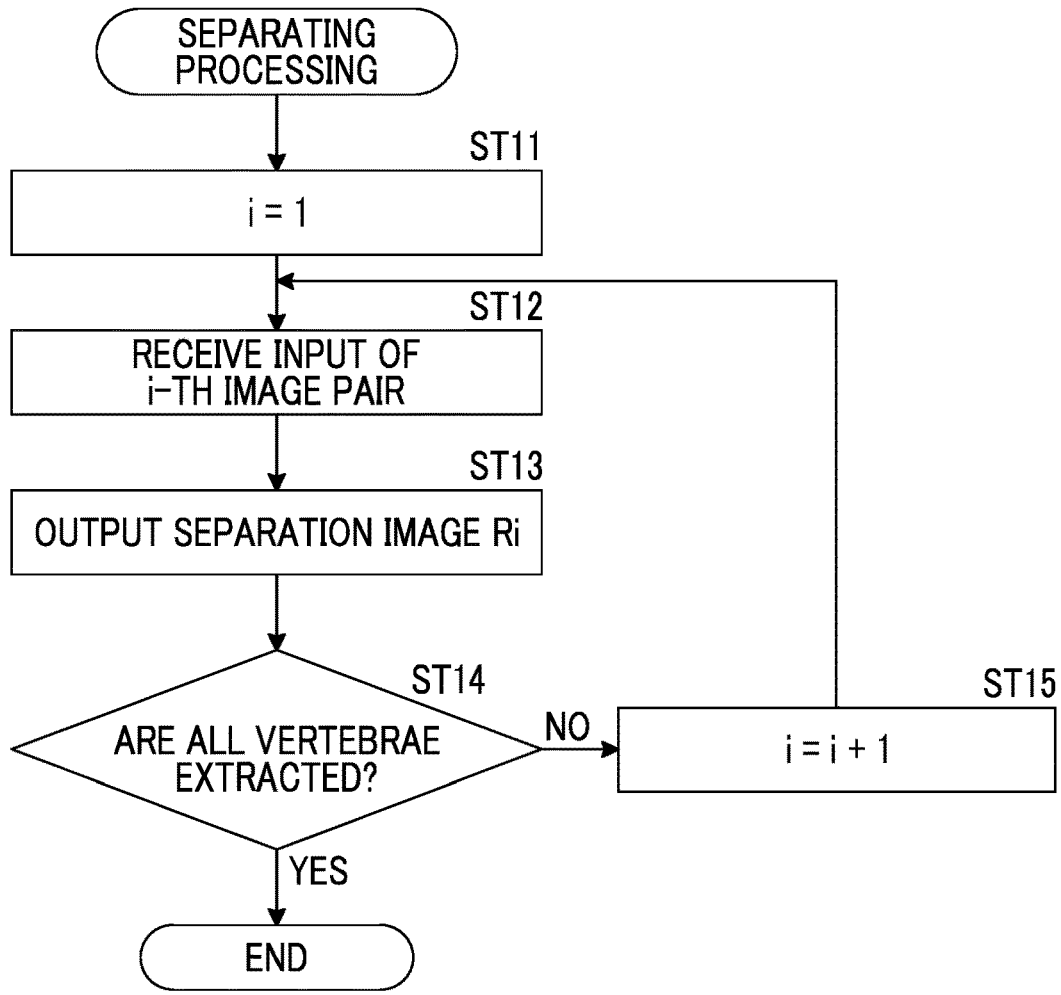
FIG. 9 is a flowchart showing separating processing in the present embodiment.

FIG. 9 is a flowchart showing the separating processing in the present embodiment. In the separating processing, 1 is first assigned to the variable for counter (Step ST11), and the input of the i-th image pair is received to the learned model M1 constituting the separation unit 23 (Step ST12). The case of i=1 is defined as the first image pair, and the first image pair includes the target image G1 and the non-separation image R0. The learned model M1 receives the input of the i-th image pair to output the separation image Ri in which i vertebrae are extracted from the target image G1 (output of the separation image Ri; Step ST13). Then, determination is made whether or not all the vertebrae are extracted in the target image G1 (Step ST14), and in a case where negative determination is made in Step ST14, 1 is added to the variable (Step ST15), and the process returns to Step ST12 and repeats the processing after Step ST12. In a case where affirmative determination is made in Step ST14, the separating processing ends. The separation image at this point becomes the separated image RF.

Returning to FIG. 8, the labeling unit 24 labels the separated vertebrae in the order of separation (Step ST4), the display control unit 25 displays the target image G1 including the labeled vertebrae on the display unit 14 (display image; Step ST5), and the process ends.

Figure 10:
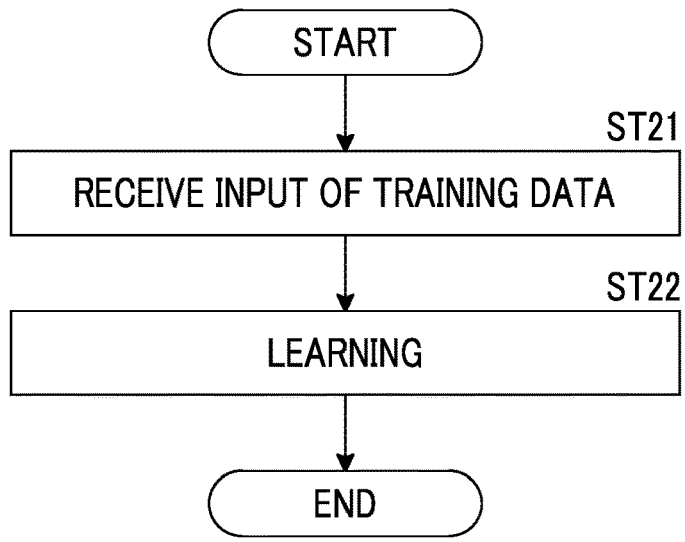
FIG. 10 is a flowchart of learning processing in the present embodiment.

FIG. 10 is a flowchart showing the learning processing. First, the learning unit 26 receives the input of the training data from the input unit 15 (Step ST21), and performs learning of the U-Net, which is a learning model, by using the training data (Step ST22). As a result, the learned model M1 is constructed.

As described above, in the present embodiment, in a case where the input of the first image pair P1 that includes the target image G1 including the plurality of vertebrae and the non-separation image R0 not including the vertebra is received, the separation image R1 in which one vertebra is extracted from the target image G1 is output. Further, in a case where the input of the new second image pair P2 including the target image G1 and the separation image R1 is received, a new separation image R2 in which another one of the vertebrae is extracted from the target image G1 is output. Furthermore, in a case where the reception of the input of the new image pair including the target image G1 and the new separation image and the output of a new separation image in which another one of the vertebrae is extracted from the target image G1 are repeated, the plurality of vertebrae included in the target image G1 are separated. Therefore, all the vertebrae can be accurately extracted even in a case where the vertebrae included in the three-dimensional image V0 do not have a predetermined size. Further, in the present embodiment, since the vertebrae are sequentially extracted, the individual vertebra can be accurately extracted even in a case where the numbers of the cervical vertebrae, the thoracic vertebrae, and the lumbar vertebrae, as well as the total number of vertebrae, differ from the number of the standard vertebral column. Accordingly, the plurality of structures, such as vertebrae, included in the three-dimensional image V0 can be accurately separated.

In the above-described embodiment, the learned model M1 included in the separation unit 23 is constituted of U-Net, but the present disclosure is not limited thereto. A support vector machine (SVM), a deep neural network (DNN), a recurrent neural network (RNN), and the like may be used.

Further, in the above-described embodiment, the target image generation unit 22 may comprise a learned model consisting of U-Net. In this case, the learned model learns to receive the input of the image including the vertebral column to output the separation image in which the cervical vertebrae, the thoracic vertebrae, and the lumbar vertebrae are separated.

In addition, in the above-described embodiment, the target image generation unit 22 is provided, but the present disclosure is not limited thereto. With no target image generation unit 22 provided, the three-dimensional image V0 including the acquired vertebral column may be used as it is, as a target image including all the vertebrae, without being classified into the cervical vertebrae, the thoracic vertebrae, and the lumbar vertebrae. In this case, all the vertebrae included in the three-dimensional image V0 are sequentially extracted, so that a separated image RF is generated.

Further, in the above-described embodiment, the vertebrae are extracted in order from the top in the target image G1, but the present disclosure is not limited thereto. In the target image G1, the vertebrae may be extracted in order from the bottom.

Further, in the above-described embodiment, the target image including the labeled vertebrae is displayed on the display unit 14, but the three-dimensional image V0 including the labeled vertebrae may be displayed on the display unit 14. As an aspect of displaying the three-dimensional image V0, any method such as volume rendering may be used.

Further, in the above-described embodiment, the target of separation is the vertebral column, but the present disclosure is not limited thereto. For example, the present embodiment may be applied to processing for sequentially separating cells by using a cell image acquired by imaging cultured cells, as a target image.

Further, in the above-described embodiment, for example, as a hardware structure of a processing unit that executes various processing such as processing performed by the image acquisition unit 21, the target image generation unit 22, the separation unit 23, the labeling unit 24, the display control unit 25, and the learning unit 26, the following various processors may be used. The various processors include, for example, a programmable logic device (PLD), such as a field programmable gate array (FPGA), which is a processor having a changeable circuit configuration after manufacture and a dedicated electrical circuit, such as an application specific integrated circuit (ASIC), which is a processor having a dedicated circuit configuration designed to perform specific processing, in addition to the CPU which is a general-purpose processor that executes software (program) to function as various processing units as described above.

One processing unit may be constituted of one of the various processors or may be constituted of a combination of two or more processors of the same type or different types (for example, a combination of a plurality of FPGAs and a combination of a CPU and an FPGA). Further, the plurality of processing units may constitute one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system on chip (SoC). As such, as the hardware structure of various processing units, one or more of the various processors are used.

Furthermore, as the hardware structure of the various processors, more specifically, an electrical circuit (circuitry) in which circuit elements, such as semiconductor elements, are combined may be used.

What is claimed is:

1. A structure separating apparatus comprising:
 a separation unit that generates a separated image in which a plurality of structures are separated, from an image including the plurality of structures,
 wherein the separation unit
  receives an input of an image pair that includes a target image relating to at least a part of the plurality of structures and a non-separation image not including the structure, to output a separation image in which one of the structures is extracted from the target image,
  receives an input of a new image pair including the target image and the separation image, to output a new separation image in which another one of the structures is extracted from the target image, and
  repeats the reception of the input of the new image pair including the target image and the new separation image and the output of a new separation image in which another one of the structures is extracted from the target image, to generate the separated image in which the plurality of structures included in the target image are separated.

2. The structure separating apparatus according to claim 1,
 wherein the separation unit has a learned model that has learned to receive an input of an image pair that includes a target image including at least a part of the plurality of structures and a non-separation image not including the structure, to output a separation image in which one of the structures is extracted from the target image,
  receive an input of a new image pair including the target image and the separation image, to output a new separation image in which another one of the structures is extracted from the target image, and
  repeat the reception of the input of the new image pair including the target image and the new separation image and the output of a new separation image in which another one of the structures is extracted from the target image, to generate the separated image in which the plurality of structures included in the target image are separated.

3. The structure separating apparatus according to claim 1, further comprising:
 a labeling unit that labels a plurality of the separated structures in an order of separation.

4. The structure separating apparatus according to claim 3, further comprising:
 a display control unit that displays the image or the target image including the labeled structure, on a display unit.

5. The structure separating apparatus according to claim 1,
 wherein the structure is a vertebra.

6. The structure separating apparatus according to claim 5, further comprising:
 a target image generation unit that classifies a plurality of the vertebrae into cervical vertebrae, thoracic vertebrae, and lumbar vertebrae, and generates the target image relating to at least one of the cervical vertebrae, the thoracic vertebrae, or the lumbar vertebrae.

7. A learning device,
 wherein the learning device receives an input of an image pair that includes a target image including at least a part of a plurality of structures and a non-separation image not including the structure, to output a separation image in which one of the structures is extracted from the target image,
 receives an input of a new image pair including the target image and the separation image, to output a new separation image in which another one of the structures is extracted from the target image, and
 repeats the reception of the input of the new image pair including the target image and the new separation image and the output of a new separation image in which another one of the structures is extracted from the target image, to generate a learned model that generates a separated image in which the plurality of structures included in the target image are separated.

8. A learned model,
 wherein the learned model receives an input of an image pair that includes a target image including at least a part of a plurality of structures and a non-separation image not including the structure, to output a separation image in which one of the structures is extracted from the target image,
 receives an input of a new image pair including the target image and the separation image, to output a new separation image in which another one of the structures is extracted from the target image, and
 repeats the reception of the input of the new image pair including the target image and the new separation image and the output of a new separation image in which another one of the structures is extracted from the target image, to generate a separated image in which the plurality of structures included in the target image are separated.

9. A structure separating method of generating a separated image in which a plurality of structures are separated, from an image including the plurality of structures, the structure separating method comprising:
 receiving an input of an image pair that includes a target image relating to at least a part of the plurality of structures and a non-separation image not including the structure, to output a separation image in which one of the structures is extracted from the target image;

receiving an input of a new image pair including the target image and the separation image, to output a new separation image in which another one of the structures is extracted from the target image; and repeating the reception of the input of the new image pair including the target image and the new separation image and the output of a new separation image in which another one of the structures is extracted from the target image, to generate the separated image in which the plurality of structures included in the target image are separated.

10. A learning method comprising:

receiving an input of an image pair that includes a target image including at least a part of a plurality of structures and a non-separation image not including the structure, to output a separation image in which one of the structures is extracted from the target image;

receiving an input of a new image pair including the target image and the separation image, to output a new separation image in which another one of the structures is extracted from the target image; and repeating the reception of the input of the new image pair including the target image and the new separation image and the output of a new separation image in which another one of the structures is extracted from the target image, to generate a learned model that generates a separated image in which the plurality of structures included in the target image are separated.

11. A non-transitory computer-readable storage medium that stores a structure separating program causing a computer to execute generating a separated image in which a plurality of structures are separated, from an image including the plurality of structures, the program causing the computer to execute:

receiving an input of an image pair that includes a target image relating to at least a part of the plurality of structures and a non-separation image not including the structure, to output a separation image in which one of the structures is extracted from the target image;

receiving an input of a new image pair including the target image and the separation image, to output a new separation image in which another one of the structures is extracted from the target image; and repeating the reception of the input of the new image pair including the target image and the new separation image and the output of a new separation image in which another one of the structures is extracted from the target image, to generate the separated image in which the plurality of structures included in the target image are separated.

12. A non-transitory computer-readable storage medium that stores a learning program causing a computer to execute:

receiving an input of an image pair that includes a target image including at least a part of a plurality of structures and a non-separation image not including the structure, to output a separation image in which one of the structures is extracted from the target image;

receiving an input of a new image pair including the target image and the separation image, to output a new separation image in which another one of the structures is extracted from the target image; and repeating the reception of the input of the new image pair including the target image and the new separation image and the output of a new separation image in which another one of the structures is extracted from the target image, to generate a learned model that generates a separated image in which the plurality of structures included in the target image are separated.

\* \* \* \* \*